US006308704B1

(12) United States Patent
Wennerberg

(10) Patent No.: US 6,308,704 B1
(45) **Date of Patent: *Oct. 30, 2001**

(54) PROCESS AND APPARATUS FOR MIXING COHESIVE POWDERS

(75) Inventor: Karin Gunilla Wennerberg, Lund (SE)

(73) Assignee: Astra Aktiebolag, Sodertalje (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/905,856

(22) Filed: Aug. 4, 1997

Related U.S. Application Data

(63) Continuation of application No. 08/433,479, filed as application No. PCT/SE95/00076 on Jan. 26, 1995, now abandoned.

(30) Foreign Application Priority Data

Feb. 2, 1994 (SE) .......... 9400335

(51) Int. Cl.[7] .......... A61M 15/00; B02C 7/00

(52) U.S. Cl. .......... 128/203.15; 128/203.12; 366/309

(58) Field of Search .......... 128/203.12, 203.15, 128/200.23, 203.16, 203.23, 203.25; 604/58; 209/366, 397, 398, 358, 320, 346, 417

(56) References Cited

U.S. PATENT DOCUMENTS

| | | | | |
|---|---|---|---|---|
| 1,162,816 | * | 12/1915 | Sperry | 209/258 |
| 1,593,312 | * | 7/1926 | Shappell | 209/358 |
| 2,534,636 | * | 12/1950 | Stirn | 128/203.15 |
| 2,569,720 | * | 10/1951 | Jesnig | 128/203.15 |
| 2,642,063 | * | 6/1953 | Brown | 128/203.15 |
| 3,512,569 | * | 5/1970 | Shen et al. . | |

(List continued on next page.)

FOREIGN PATENT DOCUMENTS

| | | | |
|---|---|---|---|
| 219114A1 | 2/1985 | (DE) | B01F/13/10 |
| D219114-A | 2/1985 | (DE) | B01F/13/10 |
| 255979A1 | 4/1988 | (DE) | A47J/31/04 |
| D255979-A | 4/1988 | (DE) | A47J/31/04 |
| 0053781 | 6/1982 | (EP) | A22C/9/00 |
| WO 95/21015 | 8/1995 | (WO) | B01F/3/18 |

OTHER PUBLICATIONS

Cartilier et al., "Effect of Drug Agglomerates Upon the Kinetics of Mixing of Low Dosage Cohesive Powder Mixtures," Drug Development and Industrial Pharmacy, 12:1911–1931, 1989.

(List continued on next page.)

*Primary Examiner*—John G. Weiss
*Assistant Examiner*—V. Srivastava
(74) *Attorney, Agent, or Firm*—Fish & Richardson P.C.

(57) ABSTRACT

The invention relates to a method of mixing cohesive finely divided powders such as finely divided powdered medicaments having a particle size less than about 10 μm comprising the combination of a rotating/vibrating movement with a sieving procedure, wherein the method comprises the steps of adding a finely divided powdered mixture of substances to a perforated partition in a container, subjecting the container to a rotational and preferably vibrating movement in horisontal and/or vertical directions whereby the rotational movement is performed in intervals and whereby the container is turned in a vertical direction an angle of substantially 180° during each turn.

The invention also includes an apparatus for mixing finely divided powders to be used in the above mentioned method as well as the use of the method according to the invention for mixing cohesive finely divided powders.

22 Claims, 2 Drawing Sheets

U.S. PATENT DOCUMENTS

| | | | | |
|---|---|---|---|---|
| 3,531,092 | * | 9/1970 | Prasehah et al. . | |
| 3,669,113 | * | 6/1972 | Altounyan et al. | 128/203.15 |
| 3,946,996 | * | 3/1976 | Gergely | 209/389 |
| 4,069,819 | * | 1/1978 | Valentine et al. | 128/203.15 |
| 4,164,476 | * | 8/1979 | Watanabe et al. | 430/137 |
| 4,983,046 | * | 1/1991 | Murata et al. | 366/312 |
| 5,243,970 | * | 9/1993 | Ambrosio et al. | 128/203.12 |
| 5,522,383 | * | 6/1996 | Calvert et al. | 128/203.15 |

OTHER PUBLICATIONS

Chowhan et al., "Mixing of Pharmaceutical Solids. I. Effect of Particle Size on Mixing in Cylindrical Shear and V–Shaped Tumbling Mixers," Powder Technology, 24:237–244, 1979.

Cooke et al., "Powder Mixing—A Literature Survey," Powder Technology, 15:1–20, 1976.

Fan et al., "Recent Development in Solids Mixing," Powder Technology, 61:255–287, 1990.

Harnby et al., "Mixing in the Process Industries," Butterworths Series in Chemical Engineering, 6 pages of Contents.

Krycer et al., "A Comparative Study of Comminution in Rotary and Vibratory Ball Mills," Powder Technology, 27:137–141, 1980.

Krycer et al., "Fine Powder Mixing in a Vibratory Ball Mill," International Journal of Pharmaceutics, 5:119–129, 1980.

Orr et al., "The Mixing of Cohesive Powders," The Chemical Engineer, 12–19, 1973.

Orr et al., "Mixing of Small Amounts of Cohesive Powders in Both Solid and Semi–Solid Systems," ChemE Symposium Series No. 64, D1–D8.

Perry, "Solid–Solid Systems," Chemical Engineers' Handbook, 5th Edition, 21–30—21–38.

Notification of Transmittal of International Preliminary Examination Report (4 pages).

Cartilier et al., "Effect of Drug Agglomerates Upon the Kinetics of Mixing of Low Dosage Cohesive Powder Mixtures," Drug Development and Industrial Pharmacy, 15(2):1911–1931, 1989.

Harnby et al., "Mixing in the Process Industries," Butterworths Series, (6 pages).

Orr et al., "The Mixing of Cohesive Powders," The Chemical Engineer, 12–19, 1973.

* cited by examiner

PROCESS AND APPARATUS FOR MIXING COHESIVE POWDERS

This is a continuation of application Ser. No. 08/433,479, filed May 10, 1995, now abandoned, which is a 371 of PCT/SE95/00076 filed Jan. 26, 1995.

FIELD OF THE INVENTION

The invention relates to a method for mixing cohesive finely divided powders, such as finely divided powdered medicaments having a particle size less than about 10 $\mu$m, and consisting of more than one substance in order to obtain a homogeneous mixture.

BACKGROUND OF THE INVENTION

Powder mixing or blending is an operation to make two or more powdered substances to form a homogeneous mixture. The operation of mixing finely divided powders consisting of two or more substances is extremely difficult as the particles are subjected to various interparticle forces and such powder can not be set in motion without an external force such as mechanical agitation, ultra sound, electrical forces or similar.

Finely-divided powders are commonly used in inhalation therapy where the size of the particles and the homogeneity of mixtures of substances are of utmost importance. Due to the fact that inhalation therapy is becoming a more and more important therapy not only in the therapy for diseases in the bronchial area but also in therapy against other diseases, the mixing of interacting powders, where a fine, cohesive ingredient may adhere to coarser carrier particles, has become a subject of increased interest during recent years. However, little work has been done regarding the situation where all the ingredients are finely divided, e.g. have a particle size smaller than 10 $\mu$m.

For finely-divided powders having a high proportion of particles with particle size smaller than about 10 $\mu$m, interparticle adhesive forces, such as van der Waal forces, make the powders cohesive, leading to the formation of irregular aggregates. This formation of aggregates makes the mixing of two or more such cohesive powders much more complicated and difficult than the mixing of powders with a particle size greater than 10 $\mu$m. Therefore, if a homogeneous mixture is required, a breakdown of the aggregates must be achieved during the mixing process.

In solid/solid mixing one of the most important requirements is to ensure uniformity of the content, which is particularly relevant for clinical effectiveness when using low dosage cohesive powder mixtures, such as for example those containing 1–2% of the active ingredient. The major problem encountered in powder mixing of finely divided powders is the inability of the commonly used mixers to break down the aggregates formed in the powder. The so-called low-power mixers are not able to breakdown the aggregates formed in the cohesive powders into their primary particles, which means that the aggregates are still present and do not permit the relative movement between particles to occur, something which is necessary if a homogeneous mixture is to be achieved. The critical step of the mixing of low dosage cohesive powder mixtures is the breakdown of the aggregates. Thus, in order to obtain a homogeneous mixture naturally formed aggregates must be repeatedly broken down. To enable the aggregates to breakdown into its primary particles a sufficiently high energy must be applied to the system.

PRIOR ART

Among the vast number of references on mixing only a few discuss the problems involving cohesive powder mixtures (particularly those with all the components being cohesive).

The following main references are of special interest:

"Powder Mixing—A Literature Survey" by M. H. Cooke et al., Powder Technology 15 (1976), 1–20, which gives a general background to the special problems involved in the technical area of mixing powders.

"Mixing in the Process Industries", edited by N. Harnby, M. F. Edwards and A. W. Nienow, Butterworths, London (1990), 375 p.

"Recent Developments in Solids Mixing" by L. T. Fan et al., Powder Technology, 61 (1990), 255–287.

JP 62,124,201 (priority date 1985) describes a process where a cohesive fine powder is sieved and mixed with a noncohesive powder in a V-type mixer. However, the fine powder was added externally to the coarse material.

Some work has also been done using rotatory and vibratory ball mills as an efficient method of mixing fine powders (I. Krycer et al., Int. J. Pharmaceutics, 6 (1980), 119–129; Powder Techn. 27 (1980), 137–141). The high energy applied in this type of milling will disrupt the crystal lattice of the particles thereby influencing the chemical and physical stability of the crystals and making the crystals more sensitive to humidity. On prolonged milling, aggregation of the minor constituent with the diluent occurs leading to cohesion and formation of an ordered mixture. Further comminution results in a fragmentation and reaggregation without loss of mixture homogeneity. However, nothing is said about the stability of the product mixture obtained.

According to N. Harnby et al. in "Mixing in the Process Industries" p. 90 a mixer for mixing cohesive powders is likely to need high shearing or impaction characteristics and could well be a particle comminuter rather than a conventional mixer. Bulk circulation of powder can be effected in fluidized beds, tumbler mixers or convective mixers and is useful when powders, which are not too cohesive, are to be mixed. The break-down of aggregates is usually accomplished by a stirring device, such as for example an impeller, which rotates at a high speed. Therefore, runner mills have been recommended where shearing mixing occurs.

The equipment employed by Orr and Shotton (Chem, Eng. No 269 (1973), 12–19 (Mixing of cohesive powders) was a Lödige Morton M4E mixer and a Y-cone mixer. The Y-cone was mounted on an Eureka rotatory machine so as to rotate about a horizontal axis.

The comprehensive review by Fan et al., referred to above, on recent developments in solids mixing covers the classification of mixing equipment, the characterisation of mixtures and the rates and mechanisms of mixing processes as well as the design and scale-up of mixers. Herein is also given a comprehensive list of references of prior work.

The commonly used equipment is further described in "Chemical Engineers' Handbook" (5th ed.) by R. H. Perry and C. H. Chilton, Tokyo, p. 21–30.

Many investigations using different methods of mixing have been performed e.g. fluidized-bed mixers. As pointed out by Fan et al. the design of mixers or blenders for particulate solids has mainly been carried out by trial and error due to the complexity of the behavior of solids when mixing and particularly with very cohesive powders.

The breakdown of aggregates and attrition are well-known phenomena and are performed by impaction (peripherical speed of the rotating internal device) or a shearing and compressing action. The attrition may produce other disturbances (size reduction etc) on batch ingredients.

The most common type of equipment for mixing in which aggregate breakers are used is the tumbler. Several different types of tumblers are available in which separate internal rotating devices for breaking down the aggregates are provided in order to minimize segregation. The form and shape of such rotating devices vary, but no reference has been found describing the use of a net in association with the use of stirring devices. The tumbler itself can not be used if an effective breakdown of the aggregates is required.

THE INVENTION

The present invention relates to another form of mixing equipment and method for the breakdown of aggregates during the mixing of cohesive particles.

The formulations in inhalation therapy require substances having a particle size being less than 10 $\mu$m. When two or more substances having this particle size are to be used in an inhalation formulation a mixing step is required. Due to the inherent properties such as for example cohesivness and aggregate formation of these powders, conventional mixing equipment is not applicable. The present invention provides a simple and effective method and apparatus for mixing finely-divided powders.

It is therefore an object of the present invention to provide a method of mixing at least two cohesive finely divided powders such as finely divided powdered medicaments having a particle size less than about 10 $\mu$m, which method comprises subjecting the powders to a rotating movement using a container with at least two compartments separated by at least one perforated partition wherein periodically the rotating movement of the container is stopped, and powder is forced from one compartment through the at least one perforated partion into at least one other compartment, as described in claim 1.

According to the invention there is also provided an apparatus for mixing cohesive finely divided powders such as finely divided powdered medicaments having a particle size less than about 10 $\mu$m in order to obtain a homogeneous mixture, which apparatus comprises a container having at least two compartments separated by at least one perforated partition, at least one of the compartments being provided with means for mixing the powders, rotation means for rotating the container from one position to a second position through an angle of rotation of 180° and by vibration means for vibrating the container before, during or after rotation whereby in use powder in one compartment is forced through the at least one perforated partition into the at least one other compartment, as claimed in claim 8.

Further preferred embodiments of the method are defined in the dependent claims 2 to 7 and preferred embodiments of the apparatus are defined in the dependent claims 9 to 17.

There is also provided an use of the apparatus for mixing cohesive finely divided powders as well as the use of a breath-actuated inhalator containing a mixture of powder produced according to the invention.

The method and apparatus of the invention have many advantages compared to prior art such as simple and cheap construction of the equipment, a totally closed system eliminating environmental and health problems (dust, allergy problems), short mixing times and a homogeneous end product. The energy input into the system is low, which eliminates any changes in crystal structure compared to diminition methods or similar methods using vibrating mills and other known processes.

BRIEF DESCRIPTION OF THE DRAWINGS

The method and apparatus according to the present invention will now be described by way of example with reference to the appended drawings, wherein.

DETAILED DESCRIPTION OF THE DRAWINGS

Figure 1:
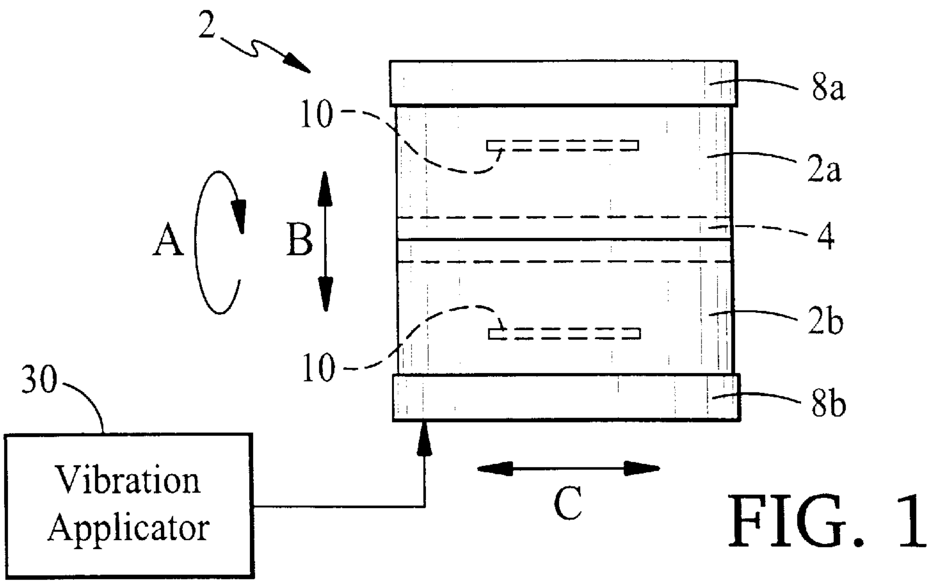
FIG. 1 shows a schematic side view of the apparatus according to the invention in the closed position.
Figure 2:
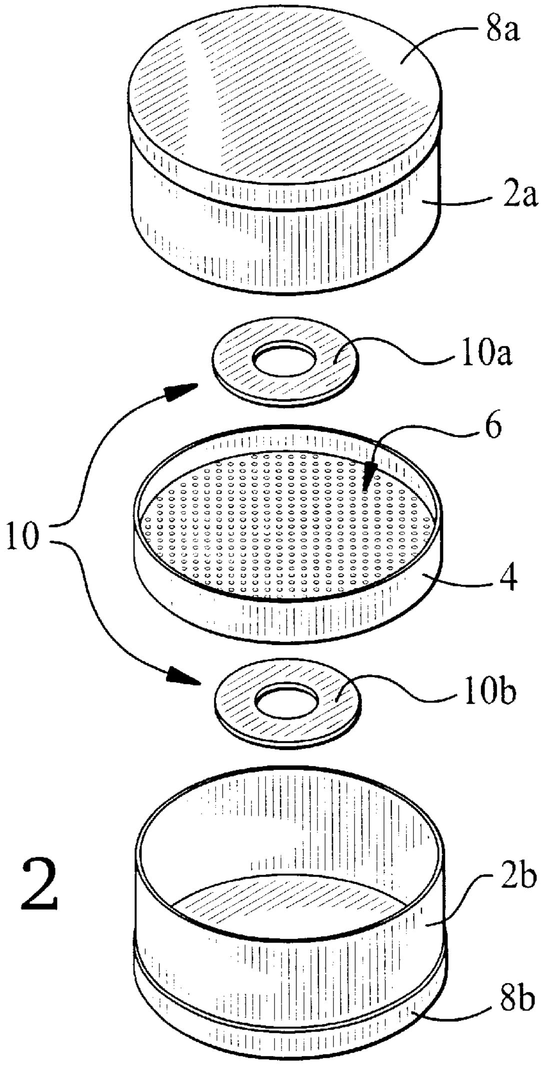
FIG. 2 shows a schematic perspective view of the apparatus in FIG. 1 with a first embodiment of the stirring device according to the invention.

The apparatus and method are now described in relation to the preferred embodiment of the device according to the invention which is schematically shown in FIGS. 1 and 2. The finely divided powder consisting of two or more substances is added to a container 2 which is divided into two compartments 2*a* and 2*b* by a partition 4. The compartments 2*a*, 2*b* are preferably of equal size but not necessarily. The partition 4 is perforated by apertures 6 (cf FIG. 2) so as to allow particles of the powder mixture to pass through the perforations after the break-down of aggregates that have been created in the powder mixture. This perforated partition 4 is preferably a net screen but any other suitable perforated wall or membrane can be used.

The perforated partition 4 is preferably a net screen made of a wire mesh having a size of the apertures 6 of less than 2 mm, preferably less than 1 mm. The size of the apertures of the wire mesh screen or the like must be fine enough to ensure that after breakdown of the aggregates the particles pass through the screen to form the finely-divided powder mixture. This breakdown of the aggregates is a requirement for ensuring homogeneous mixing.

Each compartment 2*a*, 2*b* is provided with an opening at the end remote from the partition 4. The opening is provided with a cover, such as a lid 8*a* and 8*b*, respectively, so that the compartments can be opened to add the powder to the containers and to empty them after the mixing procedure is completed. In the preferred embodiment a stirring device 10 is provided inside at least one of the compartments.

It is also possible to provide vibrations or ultra sound on the perforated partition, i.e. the net, to force the powder mixture through the perforated partition. In this case a stirring device is not necessary.

The stirring device 10 is preferably provided in a freely movable manner inside the container and during mixing the stirring device is moved within the powder mixture in one compartment as well as over the perforated partition 4 in the other compartment in order to break down the aggregates and force the powder particles through the apertures 6. The stirring device can be of any suitable type, such as for example pieces of metal or any other material, such as rings 10*a*, 10*b*, as shown in FIG. 2. The rings 10*a* and 10*b* are loose inside at least one of the compartments.

Figure 3A:
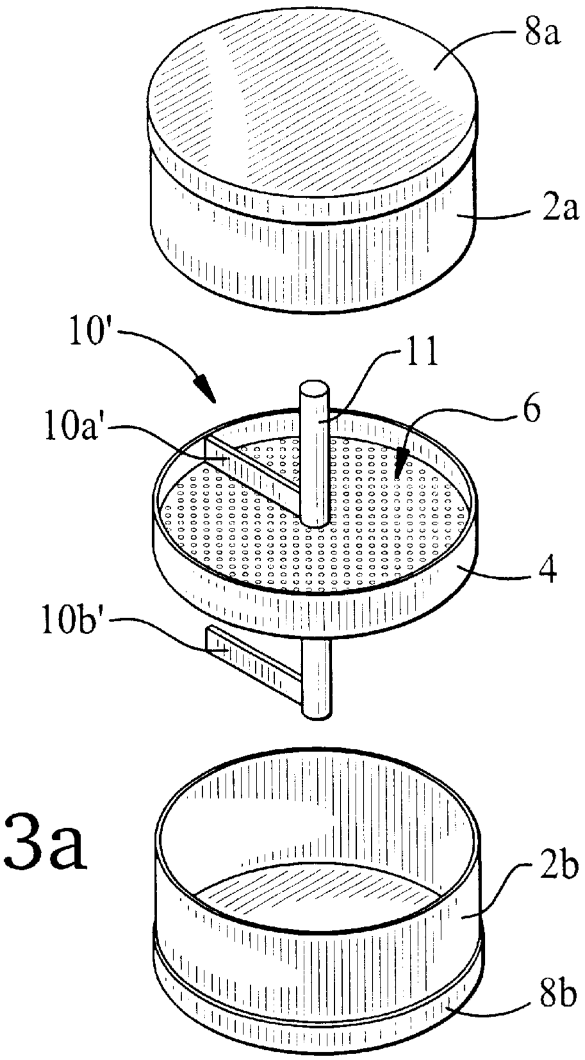
FIG. 3*a* shows a schematic perspective view of the apparatus in FIG. 1 with a second embodiment of the stirring device according to the invention.
Figure 3B:
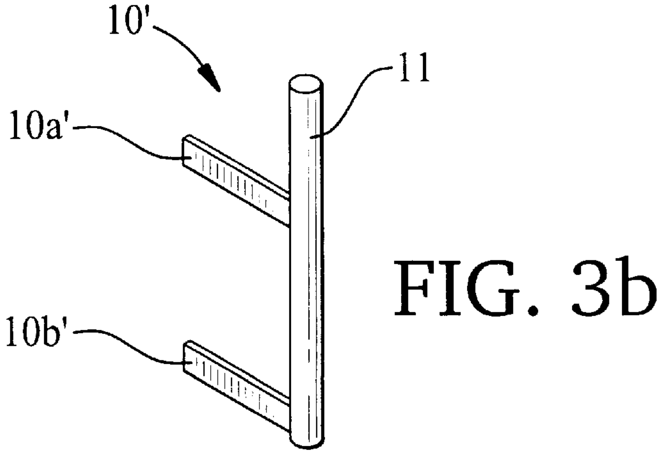
FIG. 3*b* shows a schematic side view of the second embodiment of the stirring device according to the invention.

The stirring device 10' can also be formed as scrapers or the like 10*a'*, 10*b'*, such as rotor blades, which are slidably or fixedly provided on an axis 11 mounted in a position corresponding to longitudinal axis of the container as can be seen in FIGS. 3*a* and 3*b*.

When finely-divided powders are to be mixed, the powders are placed on the partition 4 in one compartment, e.g. 2*a* of the container 2. If a loose stirring device such as rings 10*a*, 10*b*, are used they are put into place and the container is closed.

The container is placed in a device which rotates the container in a vertical direction 180° thereby turning it upside down. After each rotation the container is vibrated in at least the vertical direction, but preferably also in the horizontal direction in order to force the particles through the perforated partition 4 and facilitate the break-down of aggregates in the powder. These movements are schematically shown by the arrows in FIG. 1 arrow A indicating the rotation of the container in the vertical direction, arrow B the vibration in the vertical direction and arrow C the vibration in the horizontal direction. The device to be used for giving the container these rotating and vibrating movements could for example be a Retsch motor or any other similar device. During the turning of the container 180° the powder will be forced to pass from container 2*a* to container 2*b* through the apertures 6 of the perforated partition 4. The stirring device (10, 10'), will thereby cause a mixing of the powders and break-down of formed agggregates and force the particles through the apertures of the partition.

Rotation in a mixer, such as a cone mixer, will often cause compaction of powder in certain areas of the powder mass and due to electro-static charges, which are created in cohesive powders, powder particles adhere to the walls of the container. The stirring device must therefore be such as to avoid these problems. Tests have shown that the most effective form of the stirring device is a metal ring provided in each compartment as described above, but other forms of the stirring device are also possible. During the vibration of the device after each rotation, the ring in the uppermost compartment will force the powder down through the apertures of the partition and the ring in the lowermost compartment will be positioned at the lowermost part of the compartment and will keep the powder in motion thereby preventing the powder from sticking to the walls as well as improving the mixing effect.

Because of the creation of electro-static forces in the powder mixture between the particles and between the particles and the walls of the container, the container and the stirring device as well as the partition should preferably be made of an electrically conducting material such as metal, for example stainless steel, or be provided with an electrically conducting layer, such as a layer of metal or other similar material such as e.g. Teflon®. It is also possible to provide scrapers or the like acting on the walls when the container is rotated and/or vibrated.

The procedure of turning is then repeated by rotating the container 180° in the vertical direction back again. In this manner both sides of the net will be used causing an efficient breaking of the aggregates. During the process of repeated turnings in intervals the container is vibrated vertically and/or horisontally between the turning intervals.

In order to obtain a homogeneous mixture the procedure will have to be repeated several times. Tests have been carried out in order to determine the optimum mixing time, and number of turns necessary. The tests are described below and a summary of the results is shown in the table.

Variants in the Apparatus Described Above

The container may be constructed in different ways. A prerequisite for a container to be used in the apparatus according to the invention is that it is totally closed and rotable around an axis, such as a tumbler mixer. The container may thereby have any suitable form such as cylinder-, cube-, double-cone-, drum-, V- or U-forms.

The stirring device which is mounted in at least one, preferably all, of the compartments of the container may have any suitable form. The stirring device may be either loose, i.e. not fixed, in at least one of the compartments; it may have a ring form, or any other form such as triangular, rectangular, quadratic or elliptical. The stirring device may also be as a rotating scraper mounted on an axis provided inside at least one of the compartments. In this case the rotating scraper, such as a flat, pitched or multiple paddle, helical ribbon, anchor impeller, helical screw or any other similar form is preferably arranged to press gently against the net of the partition. The stirring devices may be either stationary or slidably/pivotably mounted on the axis.

The operation forcing the powder mixture through the apertures of the net may also be accomplished by using a stirring device with for example rotating scrapers, which are rotating and simultaneously vibrating.

The rotating and/or vibrating means could be provided with means rotating the container around its longitudinal axis.

Another modification is to provide a vibrating perforated net in order to facilitate the passage of the powder through the net, in which a stirring device is not necessary.

SUMMARY OF EXPERIMENTAL DATA FOR MIXING COHESIVE POWDERS

Possible types of container configurations include a variety of tumbling mixers, such as a cube mixer, cylinder mixers or modified cone mixers, with preferably planar ends. The size of the container could be varied from at least 100 l, down to less than 1 l. The limiting factor concerning the size is the technical handling of the powder and the rotating and/or vibrating equipment as large volumes of cohesive powders are very difficult to handle. Tests have shown that mixing will take place in an appropriate manner even if the container is large. The volumetric fill of the containers is preferably less than 30% to 40% of the total volume of the container. The final result will further depend on the geometry and design of the mixer, rotating frequency, time of mixing and nature of the substances to be mixed. The total error in powder mixing experiments observed could also be due to the analytical method, sampling, mixing and impurities. The deviation from homogeneity of the mixing of powders can by use of the present invention be less than 5%, and is more preferably less than 3%.

Description of a Method of Mixing in Accordance with the Invention

The operation was performed by placing 40 g of powders, consisting of 0.80 g (2.0%) finely divided active drug substance, e.g. salbutamol and 39.20 g finely-divided filler or carrier, e.g. lactose, both powders having a particle size <10 μm, in one of the chambers of the container (total volume 860 ml) as shown in FIG. 1. The chamber was closed and the equipment placed on a vibrating device (a Retsch motor) providing vibrational movement in both vertical and horisontal directions. The mixer was rotated manually nine (9) times during the mixing time (20 min).

After the procedure was completed 10 samples were withdrawn from different locations of the powder bed. The samples were analyzed and gave a deviation from homogeneity of 2.0%. The sample volumes were small (<10 mg) so as to avoid affecting significantly the total volume of the powder bed.

A further experiment under the same conditions but with a mixing time of 40 min and eighteen (18) manually rotations gave a deviation of homogeneity of 0.96%.

Tests have also shown that when mixing cohesive finely divided powders of active components in concentration 0.1% to 50% with another component a homogeneous mixture will be reached within 60 minutes. The selection of mixing parameters, that is the number of turns amplitude of vibration and mixing time, depends on the batch size. The table below shows a summary of results from tests which have been carried out to determine the homogeneity of the resulting mixture with various mixing times.

| Test no. | Batch size (g) | Vol. of mixing con- tainer | Number of turns | Mixing time (min) | Number of samples taken | %-Active sub- stance | RSD % |
|---|---|---|---|---|---|---|---|
| 1 | 18 | A | 9 | 16 | 5 | 31.30 | 2.90 |
| 2 | 20 | A | 9 | 12 | 3 | 27.60 | 0.90 |
| 3 | 20 | A | 9 | 20 | 3 | 6.70 | 0.10 |
| 4a | 24 | A | 3 | 5 | 4 | 1.65 | 0.70 |
| 4b | 24 | A | 9 | 20 | 4 | 1.69 | 0.40 |
| 5 | 40 | A | 9 | 16 | 3 | 2.21 | 0.74 |
| 6 | 570 (2 × 285) | B | 16 | 30 | 10 | 1.90 | 1.80 |
| 7 | 300 | B | 9 | 20 | 5 | 0.95 | 1.70 |
| 8 | 500 | C | 11 | 30 | 10 | 1.98 | 1.49 |

A = Mixing container 860 ml
B = Mixing container 4400 ml
C = Mixing container 5500 ml The method according to the invention provides efficient mixing of cohesive finely-divided ingredients on a large as well as a small scale and thereby facilitates the use or mixtures of powders in inhalation therapy, where the simultaneous inhalation of several drug substances/fillers/diluents/additives are necessary. Fillers, carriers, diluents and additives are often necessary for dosing accuracy when using very potent drug substances which have to be administered in very small doses. Other kinds of additives, such as absorption promoters may be required, in the powder mixture in order for the inhalation route of therapy to be used for substances which penetrate the tissue within the bronchial area with difficulty.

Some mixtures of powders having particles which are extremely difficult to mix may require further mixing in order to obtain a homogenous mixture. For this purpose the method according to the invention can be repeated several times. Between each mixing process the container is emptied and the powder mixture is filled into either the same or a new container.

What is claimed is:

1. A method of mixing at least two initially unmixed cohesive finely divided powders having a particle size less than about 10 $\mu$m, which method comprises:

providing a mixing device comprising a container that is closed during operation, the container having at least two compartments separated by at least one perforated partition and means for forcing a powder through the perforated partition;

placing the unmixed powders in said mixing device;

subjecting the mixing device to a rotating movement; and periodically stopping the rotating movement of the container, and forcing the powders from one compartment through the at least one perforated partition into the at least one other compartment, wherein, in addition to the rotating movement, the container before, during or after rotation is subjected also to a vibrating movement in both the vertical and horizontal directions of the container.

2. A method according to claim 1, wherein the container is rotated in a vertical direction through an angle of substantially 180° and after each such rotation powder is forced through the perforated partition.

3. A method according to claim 1, wherein at each stopping of rotation of the container substantially all of the powder is forced through the at least one perforated partition.

4. A method according to claim 1, wherein a vibration or ultra-sound is applied to the at least one perforated partition forcing the powder mixture through the perforations of the at least one perforated partition.

5. The method of claim 1 wherein the steps of the method are repeated at least once, and wherein the container is emptied before the steps of the method are repeated.

6. The method of claim 1 wherein at least one of said powders comprises a powdered medicament.

7. Apparatus for mixing cohesive finely-divided powders having a particle size less than about 10 $\mu$m in order to obtain a homogenous mixture, which apparatus comprises a container that is closed during operation and that has at least two compartments separated by at least one perforated partition, at least one of the compartments being provided with means for mixing powders and forcing powders through the perforated partition, rotation means for rotating the container from one position to a second position through an angle of rotation of 180° and by vibration means for vibrating the container movement in both the vertical and horizontal directions before, during or after rotation whereby in use powder in one compartment is forced through the at least one perforated partition into the at least one other compartment.

8. Apparatus according to claim 7, wherein the vibrating means vibrates the container when in use in both the vertical and horizontal directions.

9. Apparatus according to claim 7 or 8, wherein the mixing means provided in at least one of the compartments comprises at least one freely movable part.

10. Apparatus according to claim 7 or 8, wherein the mixing means comprises rotating scrapers provided on an axis extending through the container in a longitudinal direction.

11. Apparatus according to claim 7 or 8, wherein the compartments are provided with an opening at ends remote from the at least one partition, and a lid is placed over the openings.

12. Apparatus according to claim 7 or 8, wherein the perforated partition is a net screen.

13. Apparatus according to claim 7 or 8, wherein the perforated partition is in a form of a sieve.

14. Apparatus according to claim 11, wherein the size of the perforations in the perforated partition are smaller than 2 mm, preferably smaller than 1 mm.

15. Apparatus according to claim 7 or 8, wherein vibration or ultra-sound is applied to the at least one perforated partition.

16. An apparatus according to claim 7 or 8, wherein the container, the mixing and forcing means and the at least one perforated partition comprise a material selected to prevent the powder mixture from adhering to one or more of the following: the container, the mixing means and the at least one perforated partition.

17. Apparatus of claim 7 wherein the powders include at least one member of a group consisting of medicaments, medicament carriers, medicament fillers, medicament diluents, and medicament additives.

18. A method for mixing two or more cohesive finely divided powders comprising the steps of placing two or more cohesive finely divided powders in a device comprising a container that is closed during operation and a perforated partition defining a plurality of chambers within the container; and forcing the powders through the partition, wherein the powders are forced through the partition by at least one freely movable part dimensioned to move freely in one of said chambers when said container is moved.

19. The method of claim 18 further comprising the step of moving the container to cause movement of said freely movable part.

20. The method of claim 18 or 19 wherein said at least one freely movable part is in a form of a ring.

21. A method of mixing at least two cohesive finely divided powders having a particle size less than about 10 $\mu$m, which method comprises subjecting the powders to a rotating movement using a container that is closed during operation, the container having at least two compartments separated by at least one perforated partition wherein periodically the rotating movement of the container is stopped, and powder is forced from one compartment through the at least one perforated partition into the at least one other compartment, wherein the container is rotated in a vertical direction through an angle of substantially 180°, and after each such rotation powder is forced through the perforated partition.

22. A method for mixing two or more cohesive finely divided powders, comprising the steps of placing two or more cohesive finely divided powders in a device comprising a container that is closed during operation, a perforated partition defining a plurality of chambers within the container, and a freely moveable part dimensioned to move freely in one of said chambers when said container is moved; and forcing the powders through the partition by the movement of said freely moveable part within one of said chambers.

* * * * *